US012347069B2

(12) United States Patent
Narukiyo et al.

(10) Patent No.: US 12,347,069 B2
(45) Date of Patent: Jul. 1, 2025

(54) IMAGE PROCESSING APPARATUS, IMAGE PROCESSING METHOD AND NON-TRANSITORY COMPUTER READABLE MEDIUM

(71) Applicants: CANON KABUSHIKI KAISHA, Tokyo (JP); CANON MEDICAL SYSTEMS CORPORATION, Tochigi (JP)

(72) Inventors: Yuta Narukiyo, Tokyo (JP); Itaru Otomaru, Kanagawa (JP)

(73) Assignees: CANON KABUSHIKI KAISHA, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 337 days.

(21) Appl. No.: 17/739,662

(22) Filed: May 9, 2022

(65) Prior Publication Data

US 2022/0366537 A1 Nov. 17, 2022

(30) Foreign Application Priority Data

May 14, 2021 (JP) ................................ 2021-082419

(51) Int. Cl.
*G06T 3/60* (2024.01)
*A61B 8/08* (2006.01)
(Continued)

(52) U.S. Cl.
CPC .............. *G06T 3/60* (2013.01); *A61B 8/0883* (2013.01); *A61B 8/12* (2013.01); *A61B 8/14* (2013.01);
(Continued)

(58) Field of Classification Search
CPC ... G06T 3/60; G06T 7/70; G06T 2207/10132; G06T 2207/20081; G06T 2207/30048; A61B 8/0883; A61B 8/12; A61B 8/14
See application file for complete search history.

(56) References Cited

U.S. PATENT DOCUMENTS 5,797,844 A * 8/1998 Yoshioka ............ G01S 7/52036
600/442
6,045,508 A * 4/2000 Hossack .................. A61B 8/12
600/463

(Continued)

FOREIGN PATENT DOCUMENTS

JP 2018-140073 A 9/2018
WO 2021/050976 A1 3/2021

OTHER PUBLICATIONS

Amano, T. et al., "An Appearance Based Fast Linear Pose Estimation" MVA2009 IAPR Conference on Machine Vision Applications (May 2009) pp. 182-186, vol. 6-3.

(Continued)

*Primary Examiner* — Lewis G West
(74) *Attorney, Agent, or Firm* — Carter, DeLuca & Farrell LLP

(57) ABSTRACT

An image processing apparatus includes at least one memory storing a program, and at least one processor which, by executing the program, causes the image processing apparatus to acquire an image of a target object, and perform correction to rotate the image so that an orientation of the target object in the image aligns with a representative direction, which is determined for type of the target object.

7 Claims, 11 Drawing Sheets

(51) Int. Cl.
    *A61B 8/12*       (2006.01)
    *A61B 8/14*       (2006.01)
    *G06T 7/70*       (2017.01)

(52) U.S. Cl.
    CPC ...... *G06T 7/70* (2017.01); *G06T 2207/10132* (2013.01); *G06T 2207/20081* (2013.01); *G06T 2207/30048* (2013.01)

(56) References Cited

U.S. PATENT DOCUMENTS

| | | | | |
|---|---|---|---|---|
| 9,734,626 | B2* | 8/2017 | Jago | G06T 7/30 |
| 10,157,486 | B2 | 12/2018 | Suzuki et al. | |
| 10,268,918 | B2 | 4/2019 | Otomaru et al. | |
| 10,636,148 | B1* | 4/2020 | Chen | G06T 7/194 |
| 10,867,423 | B2 | 12/2020 | Suzuki et al. | |
| 2005/0251036 | A1* | 11/2005 | Abuhamad | A61B 8/0866 600/443 |
| 2007/0238999 | A1* | 10/2007 | Specht | A61B 8/0891 600/437 |
| 2014/0003693 | A1* | 1/2014 | Lee | G06T 7/73 382/131 |
| 2015/0016704 | A1* | 1/2015 | Weese | G06T 7/73 382/131 |
| 2015/0281509 | A1* | 10/2015 | Legakis | G06V 20/40 348/231.2 |
| 2015/0302638 | A1* | 10/2015 | Jago | G06T 7/30 345/420 |
| 2016/0095581 | A1* | 4/2016 | Yoneyama | A61B 8/4254 600/440 |
| 2016/0174902 | A1* | 6/2016 | Georgescu | G06V 10/454 600/408 |
| 2020/0210717 | A1* | 7/2020 | Hou | G06V 20/588 |
| 2020/0210769 | A1* | 7/2020 | Hou | G06F 18/211 |
| 2021/0118157 | A1* | 4/2021 | LeGendre | G06T 7/90 |
| 2021/0137634 | A1* | 5/2021 | Lang | A61B 90/98 |
| 2022/0230346 | A1 | 7/2022 | Otomaru et al. | |
| 2022/0277592 | A1* | 9/2022 | Hosono | G06T 3/60 |
| 2022/0284584 | A1* | 9/2022 | Lee | G06V 10/82 |
| 2022/0304653 | A1* | 9/2022 | Smistad | A61B 8/10 |

OTHER PUBLICATIONS

Notice of Reasons for Refusal issued by the Japanese Patent Office on Nov. 26, 2024 in corresponding JP Patent Application No. 2021-082419, with English translation.

* cited by examiner

PROBE ANGLE = 0°

PROBE ANGLE = 90°

IMAGE PROCESSING APPARATUS, IMAGE PROCESSING METHOD AND NON-TRANSITORY COMPUTER READABLE MEDIUM

BACKGROUND OF THE INVENTION

Field of the Invention

The present disclosure relates to an image processing apparatus, an image processing method, and a non-transitory computer readable medium.

Description of the Related Art

In medical fields, diagnosis is performed using medical images acquired by various image diagnostic apparatuses (modality), such as an ultrasonic image diagnostic apparatus. In such diagnosis, a technique of imaging a target space all at once using a three-dimensional ultrasonic probe is performed, and the target object is analyzed using the captured three-dimensional image, whereby the movement and functions of the target object can be observed.

In order to analyze the target object based on a three-dimensional image, a characteristic plane (called "standard plane") used for the analysis has to be estimated (identified), but the operation to estimate the standard plane in the three-dimensional image imposes an extra workload on the operator. Therefore to reduce the workload accompanying the estimation of a standard plane in an image, various techniques to automatically estimate the plane in the image have been proposed.

Japanese Patent Application Publication No. 2018-140073 discloses a technique to estimate and correct the orientation of a target object in a three-dimensional image captured by trans-esophageal echocardiography, based on the probe angle of a probe used for the image capturing. According to Japanese Patent Application Publication No. 2018-140073, it is estimated which of a four-chamber view and a two-chamber view is drawn on an observation surface on the basis of the probe angle, using a relationship between the probe angle and a type of plane drawn on the observation surface.

By differentiating an axial inversion pattern between the case of the four-chamber view and the case of the two-chamber view, the orientation of the target object in the three-dimensional image after the axial inversion can be aligned. In other words, the orientation of the target object (type of plane drawn on the observation surface) in the three-dimensional image is determined based on the probe angle, whereby the orientation of the target object is aligned.

SUMMARY OF THE INVENTION

According to an aspect of the present disclosure, it is provided an image processing apparatus including at least one memory storing a program, and at least one processor which, by executing the program, causes the image processing apparatus to acquire an image of a target object, and perform correction to rotate the image so that an orientation of the target object in the image aligns with a representative direction, which is determined for type of the target object.

In addition, according to an aspect of the present disclosure, it is provided an image processing apparatus including at least one memory storing a program, and at least one processor which, by executing the program, causes the image processing apparatus to acquire an image of a target object, and estimate a standard plane based on the image, in a search range that is set in accordance with an orientation of the target object in the image.

The present disclosure may be regarded as an image processing method that includes at least a part of the above mentioned processing, a program that causes a computer to execute this method, or a non-transitory computer readable recording medium that stores this program. The present invention may be implemented by combining the above mentioned configurations and processing operations as long as there is no technical inconsistency.

Further features of the present invention will become apparent from the following description of exemplary embodiments with reference to the attached drawings.

DESCRIPTION OF THE EMBODIMENTS

Figure 1:
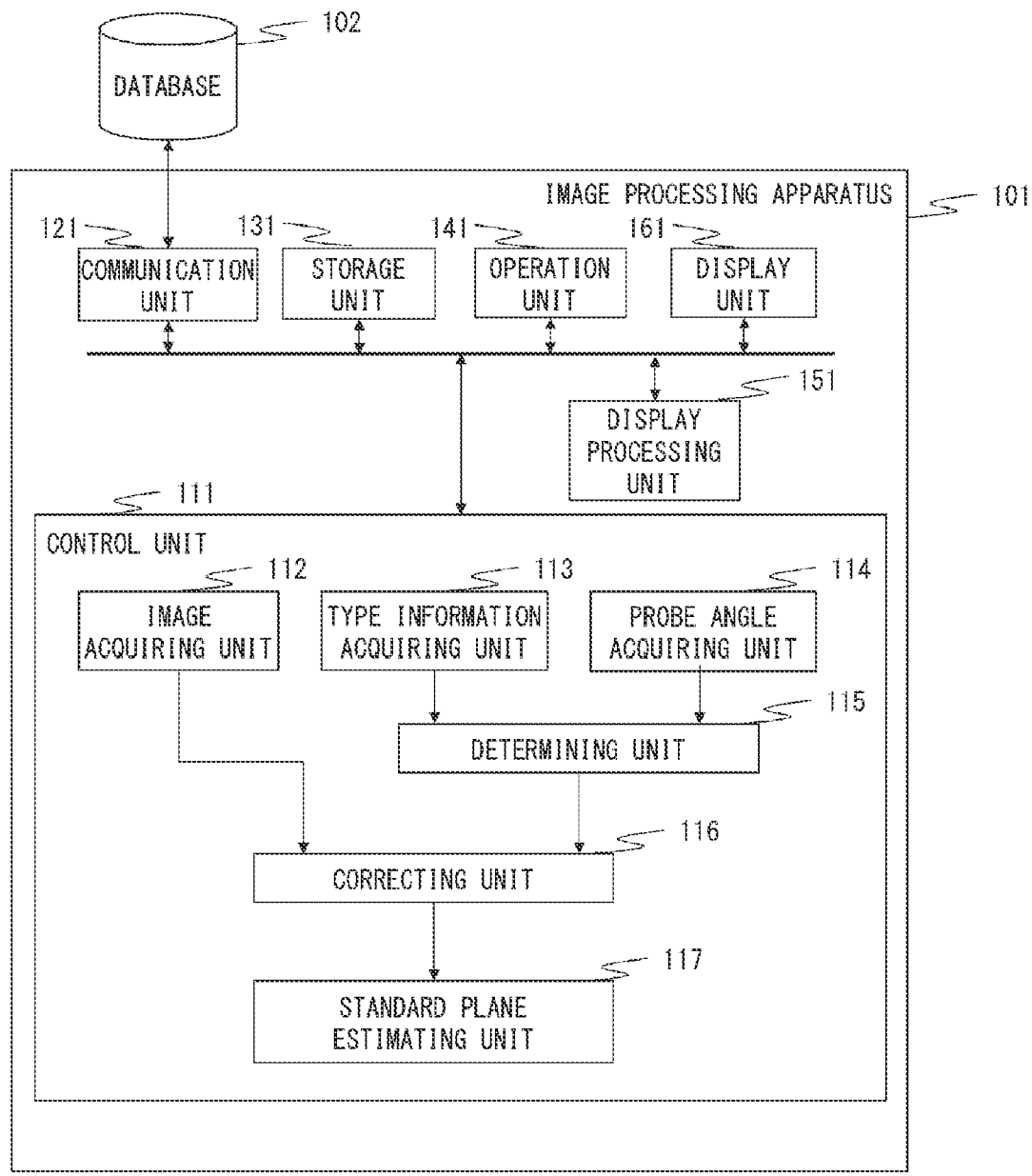
FIG. 1 is a block diagram depicting a configuration example of an image processing system according to an embodiment.

According to the above mentioned prior art, in a case where a plurality of types of target objects are imaged using a probe, an appropriate standard plane may not be estimated for each target object.

With the foregoing in view, it is an object of the present disclosure to provide a technique to correct an image by determining the orientation of a target object in an image in accordance with the type of the target object.

An embodiment of the present disclosure will be described with reference to the drawings. The present disclosure, however, is not limited to the following embodiment, but may be modified as needed within a scope not departing from the spirit thereof. In the drawings described below, a composing element having a same function is denoted with a same reference sign, and description thereof may be omitted or simplified. For example, a plane may be a twisted polar cross-section (curved slice).

In an operation to estimate a standard plane in a three-dimensional image acquired by image capturing using a probe, the search range needs to be expanded in a constraint-free state (state where orientation of the target object in the three-dimensional image is unknown). For example, the search range in this case is 360° in the circumferential direction with a certain axis as a center. On the other hand, if there is a constraint in the orientation of a target object in the three-dimensional image, a constraint can be set to search the standard plane (that is, the search range can be limited).

Comparing the trans-esophageal echocardiography that images a target object using a probe via the esophagus and the trans-thoracic echocardiography that images a target object from the body surface side, the same target object is imaged in a state where the vertical and horizontal positional relationships are inverted because the imaging directions are different. In this inverted state of the captured images, the correction direction can be uniquely determined if the images are two-dimensional images. However, in the case of three-dimensional images, in addition to correction in the vertical direction, it must be determined which of the horizontal direction and the depth direction is inverted for correction in accordance with the orientation of the target object in the three-dimensional image (the orientation determined by the type of the plane (cross-section) drawn on the observation surface in the three-dimensional image).

In the case of the above mentioned prior art, if a plurality of target objects are included in a three-dimensional image, it may be difficult to specify an appropriate correction direction for each target object. According to the technique of the present disclosure, however, in the three-dimensional image, the orientation of the target object can be appropriately determined m accordance with the type of the target object.

In an imaging processing apparatus according to an embodiment described below, it is assumed that a mitral valve or an aortic valve of a heart is observed using a three-dimensional ultrasonic image.

First Embodiment

An image processing apparatus according to First Embodiment acquires a three-dimensional ultrasonic image as an input image, which a user (e.g. physician, technician) captures using an ultrasonic probe for trans-esophageal echocardiography. The image processing apparatus also acquires information on the rotation angle of a scanning surface of the ultrasonic probe when the input image was captured, and information on the type of a target object (information on whether the inspection target is a mitral valve or an aortic valve) specified by the user. Then the information processing apparatus determines the orientation of the target object in the input image based on the acquired input image and the information.

The orientation of the target object in the input image is a relative positional relationship between the imaging direction when imaging is performed using an ultrasonic probe and the target object, and is determined based on the type of the standard plane of the target object drawn on the observation surface in the input image. Therefore the orientation of the target object and a type of the standard plane drawn on the observation surface are corresponded. The type of the standard plane of the target object includes a "representative plane (cross-section)" (also called "representative standard plane") used for observing the target object, and a "non-representative plane (cross-section)" (also called "non-representative standard plane") that is different from the representative plane. The type of the orientation of the target object includes a "representative direction", which is an orientation of the target object when the target object is disposed such that the representative plane of the target object is drawn on the observation surface in the input image, and a "non-representative direction", which is an orientation of the target object when the target object is disposed such that the non-representative plane is drawn on the observation surface in the input image.

Based on the determined type of orientation of the target object, the image processing apparatus performs rotational correction on the input image, so that the orientation of the target object of the input image is aligned with the representative direction. In other words, the image processing apparatus performs rotation processing on the input image in which a non-representative plane is imaged as an observation surface, so that the representative plane becomes the observation surface. Further, in order to learn an identifier that estimates the standard plane in the input image, the image processing apparatus generates data required for the learning using the determined type of the orientation of the object. The image processing apparatus also estimates a standard plane using the identifier in the input image in which the orientation of the target object is aligned with the representative direction, and displays an image of the estimation result which the user can visually recognize. The processing steps executed by the image processing apparatus will be described in detail later.

The configuration and processing of the image processing apparatus according to the present embodiment will be described with reference to FIG. 1. FIG. 1 is a block diagram depicting an example of a general configuration of an image processing system that includes the image processing apparatus 101 according to the present embodiment. As indicated in FIG. 1, the image processing apparatus 101 includes: a control unit 111, a communication unit 121, a storage unit 131, an operation unit 141, a display processing unit 151 and a display unit 161. The image processing apparatus 101 is connected to an external database 102 via the communication unit 121.

The control unit 111 is constituted of a central processing unit (CPU) and a dedicated or general purpose processor. The control unit 111 may also be constituted of a graphic processing unit (GPU), a field-programmable gate array (FPGA) and the like. Furthermore, the control unit 111 may be constituted of an application specific integrated circuit (ASIC) or the like.

An image acquiring unit 112 acquires an input images from the database 102 or a storage unit 131. The input image is an image of the target object of a test subject (patient) acquired by an ultrasonic diagnostic apparatus, for example, and in the present embodiment, the input image is a three-dimensional image capturing a mitral valve or an aortic valve, as a target object, for example. The image acquiring unit 112 may acquire an input image directly from the diagnostic apparatus, and in this case, the image processing apparatus 101 may be installed in the diagnostic apparatus as a part of the functions of the diagnostic apparatus. In the present embodiment, an input image is assumed to be a three-dimensional image in a one-time phase, but may be a moving image in a plurality of time phases, or a plurality of three-dimensional images or three-dimensional moving images.

A type information acquiring unit 113 acquires the type information on the target object (analysis target) in the input image from the database 102, the storage unit 131 or the operation unit 141. In the present embodiment, the type information acquired by the type information acquiring unit 113 is information to identify whether the target object is a mitral valve or an aortic valve. This type information may be added as meta information of an input image acquired by the image acquiring unit 112.

A probe angle acquiring unit 114 acquires a rotation angle of the ultrasonic probe on the scan surface (hereafter called "probe angle") when the input image was captured, from the database 102, the storage unit 131 or the operation unit 141. The information on the probe angle may be attached as the meta information of the input image acquired by the image acquiring unit 112.

A determining unit 115 determines the type of the orientation of the target object in the input image based on the information on the type of the target object acquired by the type information acquiring unit 113 and the information on the probe angle acquired by the probe angle acquiring unit 114. In the present embodiment, for the type of the orientation of the target object, the determining unit 115 determines whether the orientation of the target object corresponds to a "representative direction" or one or more "non-representation directions". The type of orientation of the target object is a concept to indicate whether the orientation of the target object is generally in the "representative direction" or in the "non-representative direction". In the case where a plurality of "non-representative directions" exist, the type of the orientation of the "non-representative direction" is also determined. The method of determining the type of the orientation of the target object will be described in detail later.

A correcting unit 116 performs rotational correction on an input image based on the type of the orientation of the target object determined by the determining unit 115, so that the orientation of the target object in the input image aligns with the representative direction. In other words, the correcting unit 116 performs the correction if the type of the orientation of the target object determined by the determining unit 115 is the non-representative direction, and does not perform the correction if the type of the orientation of the target object is the representative direction. The rotational correction on the input image may be a correction to align the orientation of the target object with the non-representative direction. In this case, the correcting unit 116 performs the rotational correction on the input image, for which the determining unit 115 determined that the type of the target object is the representative direction, so that the orientation of the target object aligns with the non-representative direction. In the case where a plurality of non-representative directions exist, the rotational correction is performed in accordance with the type of the orientation of the non-representative direction determined by the determining unit 115. The rotational correction on the input image will be described in detail later.

A standard plane estimating unit 117 acquires the image after the correcting unit 116 performed the rotational correction, and estimates a standard plane based on the acquired image. The estimation of the standard plane will be described in detail later.

The communication unit 121 is connectable to an external device and a network, so as to implement communication with the external device and the network using predetermined communication means. The communication unit 121 may be constituted of a wireless device that accesses Wi-Fi, Bluetooth. or the like, or may be constituted of a cable device of a cable local area network (LAN) or universal serial bus (USB). The communication unit 121 acquires various data, such as image data or learning data, by communicating with the external database.

The storage unit 131 is constituted of at least one medium to record data, such as a hard disk drive (HDD) and a random access memory (RAM), and is used for saving various data and is a primary storage for various calculation results, for example. The storage unit 131 may be constituted of a main storage, which is a volatile memory for temporarily storing read data and the like, and as an auxiliary storage that stores data long term.

The operation unit 141 is constituted of such input devices as a keyboard, a mouse, a touch panel and a remote controller, and receives an instruction inputted by the user and outputs the received instruction to various devices.

The display processing unit 151 processes the image and calculation result received from the control unit 111 in a format that the display unit 161 can display, and outputs the processing result to the display unit 161.

The display unit 161 is constituted of such an output device as a display, and displays such display data as a calculation result and various images processed by the display processing unit 151.

The database 102 stores various data used for processing by the image processing apparatus 101. The database 102 may store images processed by the image processing apparatus 101, or store learning models used by the standard plane estimating unit 117, or store a calculation result and output images from the image processing apparatus 101. The database 102 may be on an external network of the image processing apparatus 101, or may be configured as a device which is physically connected to the image processing apparatus 101.

Figure 2:
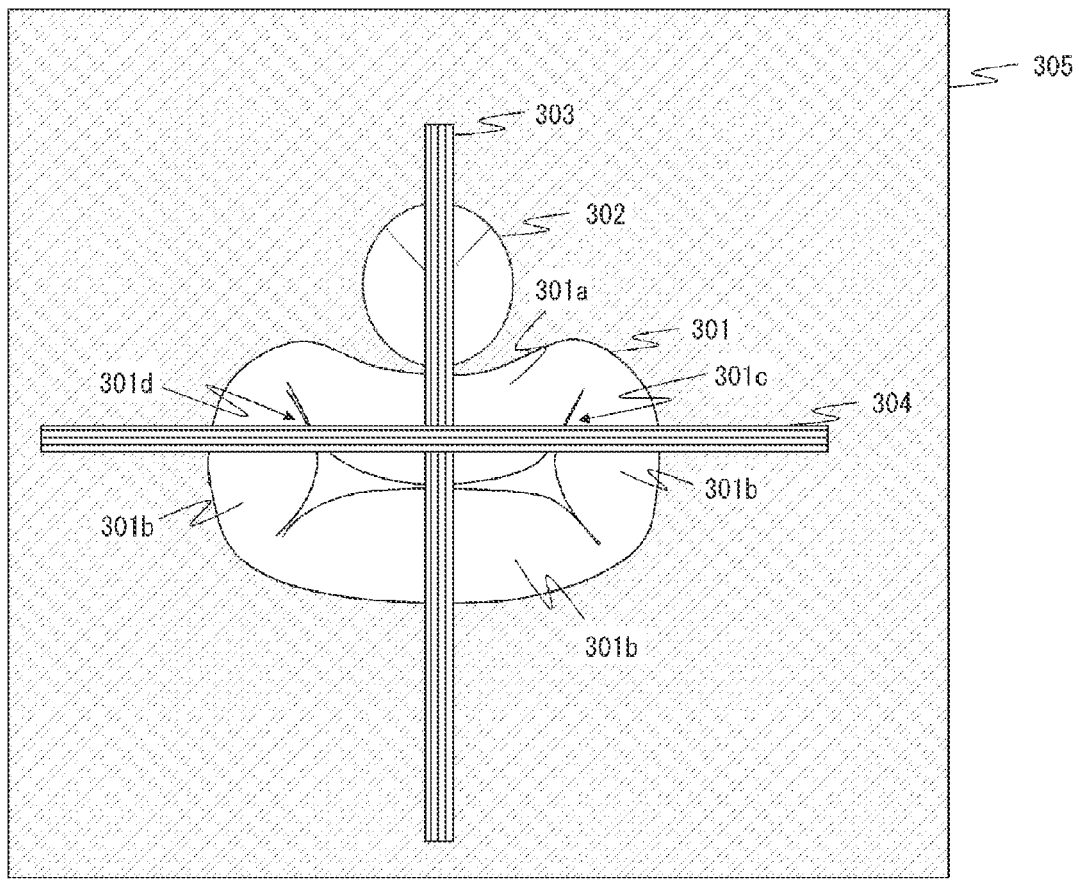
FIG. 2 is a schematic diagram depicting a mitral valve analysis by trans-esophageal echocardiography according to an embodiment.

Here a three-dimensional image captured by trans-esophageal echocardiography in the present embodiment will be described. FIG. 2 is a schematic diagram depicting a mitral valve analysis by trans-esophageal echocardiography. A mitral valve 301 is divided into an anterior cusp 301a and a posterior cusp 301b. An aortic valve 302 exists near the mitral valve 301, but these values are not always disposed in parallel in the direction shown on paper as indicated in FIG. 2, and the directions of the openings of these valves are not always the same. This means that a plurality of standard planes exist when each valve is observed.

The standard plane in the mitral valve analysis to observe a mitral valve will be described first. A first standard plane in the mitral valve analysis is a standard plane 303, which is a long axis surface that includes approximate centers of the mitral valve 301 and the aortic valve 302. A second standard plane in the mitral valve analysis is a standard plane 304, which is a long axis surface that includes a line passing through the two connecting positions 301c and 301d of the anterior cusp 301a and the posterior cusp 301b of the mitral valve 301, and is approximately orthogonal to the standard plane 303. Generally the center portion of the anterior cusp 301a and both ends of the posterior cusp 301b are imaged if the standard plane 304 is used. A third standard plane in the mitral valve analysis is a standard plane 305 which is a short axis surface that includes the center of the mitral valve 301 and is approximately orthogonal to the standard plane 303 and the standard plane 304.

Figure 3:
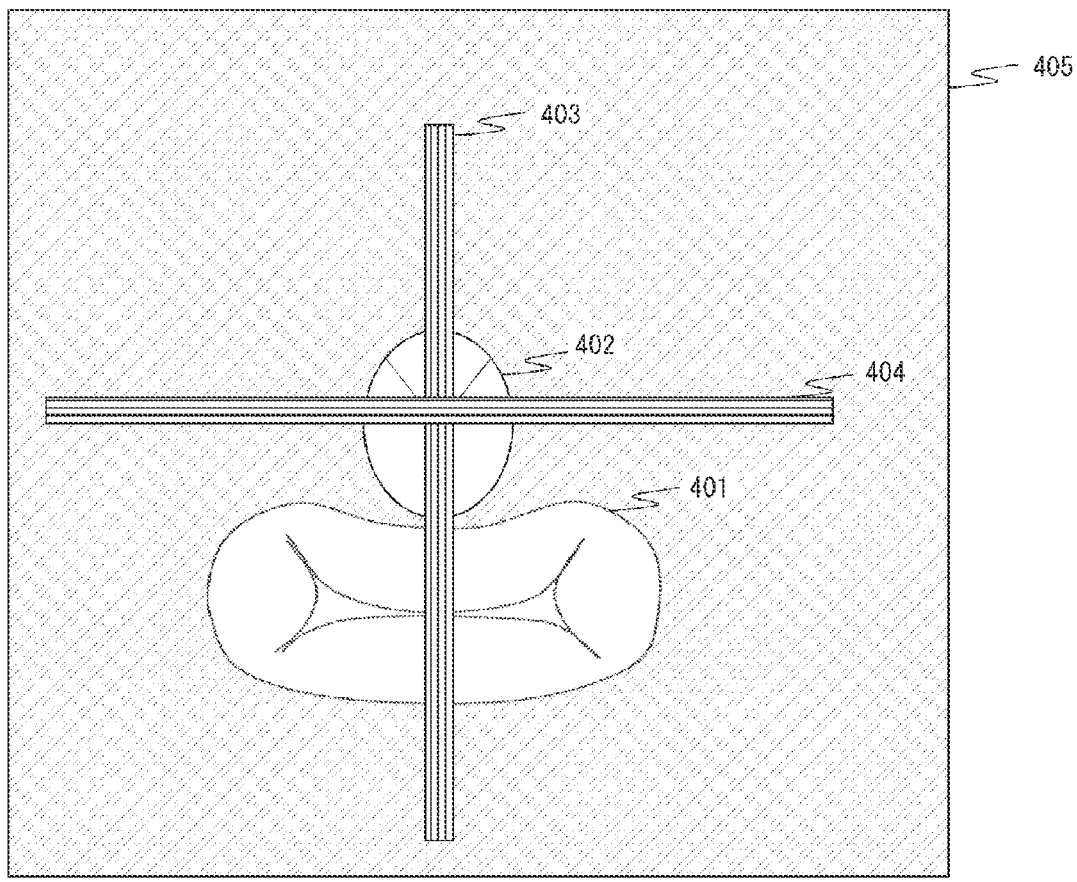
FIG. 3 is a schematic diagram depicting an aortic valve analysis by trans-esophageal echocardiography according to an embodiment.

The standard plane in the aortic valve analysis to observe the aortic valve will be described next. FIG. 3 is a schematic diagram depicting the aortic valve analysis by trans-esophageal echocardiography. A first standard plane in the aortic valve analysis is a standard plane 403, which is a long axis surface that includes approximate centers of the mitral valve 401 and the aortic valve 402. The standard plane 403 may be the same surface as the standard plane 303 in the mitral valve analysis. A second standard plane in the aortic valve analysis is a standard plane 404, which is a long axis surface that includes a center of the aortic valve 402, and is approximately orthogonal to the standard plane 403. A third standard plane in the aortic valve analysis is a standard plane 405, which is a short axis surface that includes the center of the aortic valve 402, and is approximately orthogonal to the standard plane 403 and the standard plane 404.

In the mitral valve analysis and the aortic valve analysis, information to check the functions of each valve can be acquired by observing the image using the above standard planes. The imaging position of the three-dimensional image in the aortic valve analysis is likely to be different from the imaging position in the mitral valve analysis mentioned above. However, if all the target objects to be analyzed are captured in the image in the analyzable state, the same imaging position as the imaging position in the mitral valve analysis may be used.

Figure 4:
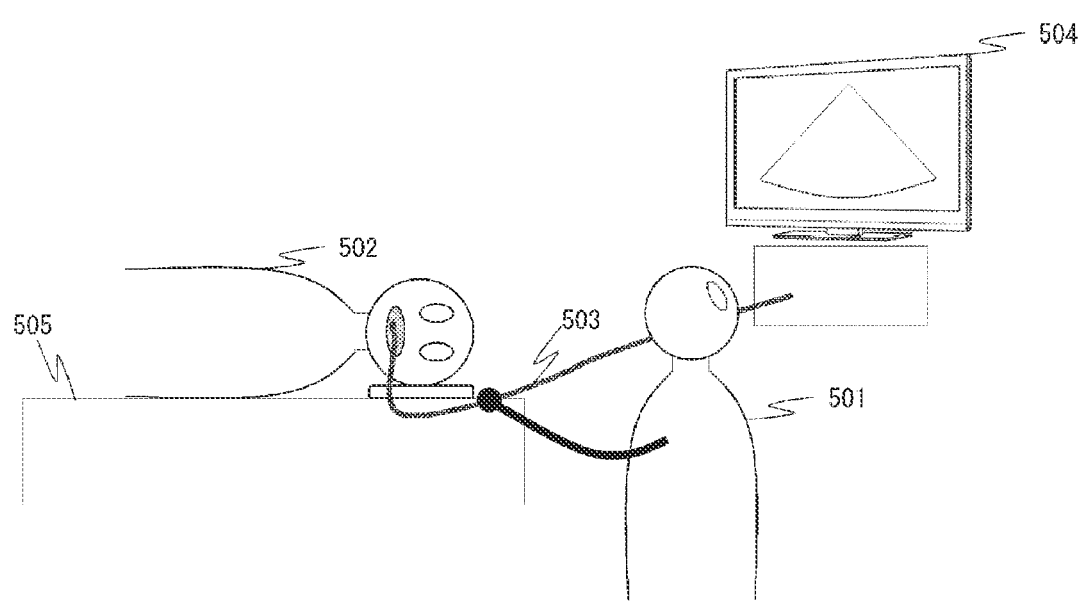
FIG. 4 is a diagram depicting an overview of trans-esophageal echocardiography according to an embodiment.

Trans-esophageal echocardiography according to the present embodiment will be described next. FIG. 4 is a schematic diagram depicting an example of the trans-esophageal echocardiography according to the present embodiment. As illustrated in FIG. 4, a user 501 (e.g. physician, technician) inserts a probe 503 into a test subject (patient) 502 via a mouth or nose, and observe the heart based on an image captured by the probe 503 through the esophagus. Here the test subject 502 may be a doll created to simulate a human body structure for training. The probe 503 assumed here is an ultrasonic probe (three-dimensional probe) that can capture a three-dimensional image, for example. However, the probe 503 may be an ultrasonic probe (two-dimensional probe) that can capture a two-dimensional image, and in this case, a three-dimensional image can be captured by rotating the probe inside the esophagus.

While observing the image displayed on a display 504 of the inspection device, the user 501 moves the end portion of the probe 503 to the position where the target object can be imaged well. At this time, the user 501 operates the probe 503 while observing the image of one plane (cross-section, observation surface) in the three-dimensional image displayed on the display 504. Specifically, the user 501 manipulates the position of the end portion of the probe 503 and the probe angle in the esophagus, so that a desired standard plane of the target object is displayed as the observation surface. Here the probe angle is a rotation angle of the scan face of the probe 503. Normally the scan face is rotated in a 0° to 180° range. In the case of the two-dimensional probe, the captured image changes depending on the rotation angle. In the case of the three-dimensional probe, the captured image is the same regardless the rotation angle, but the observation surface during inspection is changed by the rotation angle, similar to the case of the two-dimensional probe.

As described with reference to FIGS. 2 and 3, in the mitral valve analysis and the aortic valve analysis using the three-dimensional ultrasonic images, mainly three standard planes to be the observation surfaces exist respectively. For example, in the mitral valve analysis according to the present embodiment, the standard plane 303 is normally imaged as the observation surface, but in some cases, the standard plane 304 may be imaged as the observation surface, depending on the individual differences of the test subjects 502 and the procedure. In other words, the standard plane 303 is the "representative plane" and the standard plane 304 is the "non-representative plane" in the case where the target object is the mitral valve.

In the aortic valve analysis, on the other hand, the standard plane 403 is normally imaged as the observation surface, but in some cases, the standard plane 405 may be imaged as the observation surface, depending on the individual differences of the test subjects 502 and the procedure. The mitral valve and the aortic valve are not parallel, and the positions and orientations thereof are different from each other, hence the user 501 adjusts the position of the probe 503 so that the aortic valve is disposed at the center of the observation surface in the image displayed on the display 504. If the probe angle of the probe 503 is set to about 25° to 45°, the standard plane 405 (short axis surface) is observed instead of the standard plane 404. In other words, in the aortic valve analysis in the present embodiment, the standard plane 403 is the "representative plane and the standard plane 405 is the "non-representative plane" in the case where the target object is the aortic valve.

Figure 5:
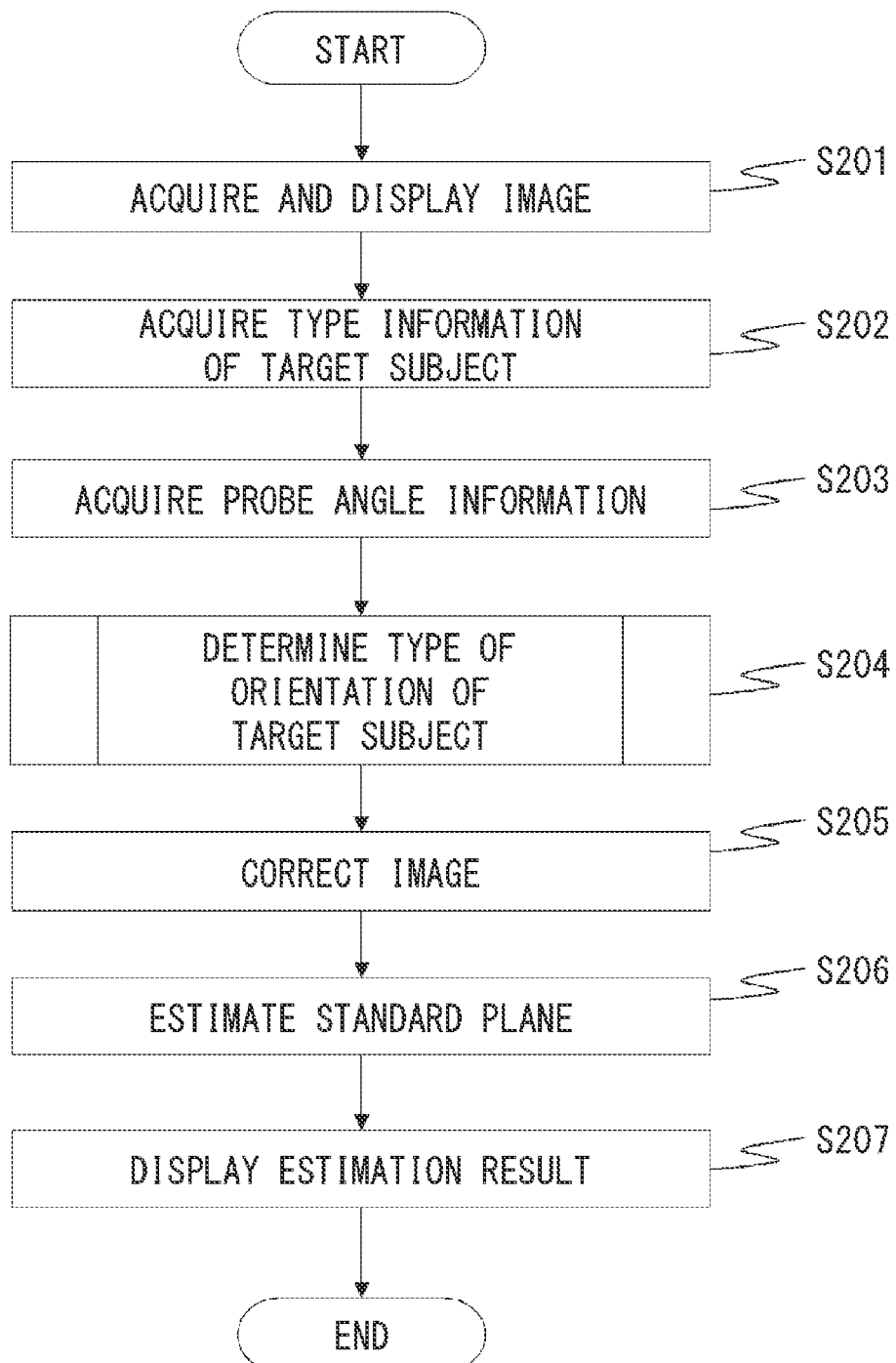
FIG. 5 is a flow chart of the processing steps executed by an image processing apparatus according to an embodiment.

An example of the processing steps executed by the image processing apparatus 101 will be described next with reference to the flow chart in FIG. 5. For example, when the power of the image processing apparatus 101 is turned ON, the CPU of the image processing apparatus 101 starts the processing in the flow chart in FIG. 5. Here, before the image processing apparatus 101 executes the processing steps described below, the user moves the probe 503 into the esophagus of the test subject 502, as illustrated in FIG. 4, and manipulates the probe 503 to perform imaging for the trans-esophageal echocardiography. Thereby a three-dimensional image (input image) of the test subject 502 based on the trans-esophageal echocardiography is acquired, and the input image is stored in the storage unit 131 of the image processing apparatus 101 and/or the database 102. In the following description, it is assumed that the input image is stored in the storage unit 131 of the image processing apparatus 101.

(Step S201: Acquire and Display Image) In step S201, the user 501 operates the operation unit 141 of the image processing apparatus 101 and specifies the input image to be used for analysis. The image acquiring unit 112 acquires the input image, which the user specified using the operation unit 141, from the storage unit 131. Here the display processing unit 151 may display the acquired image on the display unit 161. In a case of a three-dimensional image of one time phase, one or more planes (cross-sections), such as an observation surface, may be displayed as the input image to be displayed, or a plane (cross-section) of an arbitrary time phase, such as an initial plane (cross-section), may be displayed. For example, in the case of the mitral valve analysis, the display processing unit 151 may display a plane (cross-section) orthogonal to each axis direction with respect to the observation surface on the display unit 161. In a case where three-dimensional images of two or more time phases are displayed, the display processing unit 151 may simultaneously display planes (cross-sections) of the plurality of time phases in the same coordinates on the display unit 161.

(Step S202: Acquire Type Information of Target Object) In step S202, the type information acquiring unit 113 acquires the type information of the target object in the image acquired by the image acquiring unit 112. In the present embodiment, as the type information, the type information acquiring unit 113 acquires the information to determine whether the target object is the mitral valve or the aortic valve from the meta information of the input image stored in the storage unit 131, for example. It is also possible that the user 501 specifies the type information of the target object using the operation unit 141, and the type information acquiring unit 113 acquires the specified type information.

(Step S203: Acquire Probe Angle Information) In step S203, the probe angle acquiring unit 114 acquires information on the probe angle of the probe when the image acquiring unit 112 captured the acquired input image. In the present embodiment, the probe angle acquiring unit 114 acquires the information on the probe angle when the input image was captured from the meta information of the input image stored in the storage unit 131. It is also possible that the user 501 specifies the information on the probe angle using the operation unit 141, and the probe angle acquiring unit 114 acquires the specified information on the probe angle.

Figure 6:
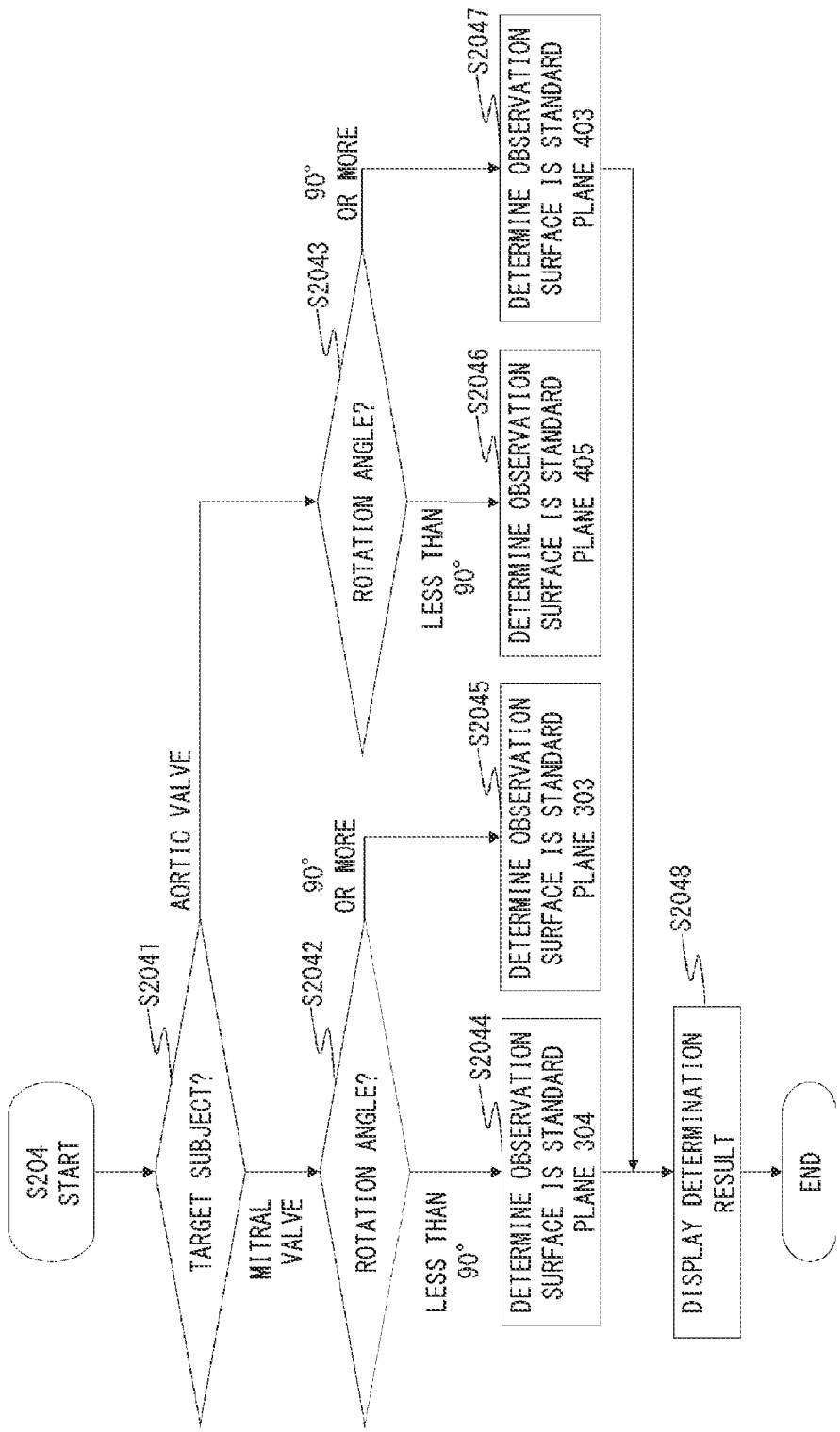
FIG. 6 is a flow chart of the processing steps to determine a standard plane according to an embodiment.

(Step S204: Determine Type of Orientation of Target Object) In step S204, the determining unit 115 determines the type of the orientation of the target object in the input image by determining which standard plane corresponds to the observation surface in the input image. In other words, the determining unit 115 determines which one of the orientations, including at least the "representative direction" and at least one "non-representative direction", is the type of the orientation of the target object. The processing steps to determine the standard plane of the input image, which the determining unit 115 executes, will be described with reference to the flow chart in FIG. 6. FIG. 6 is an example of the processing of the sub-routine of step S204 in FIG. 5.

(Step S2041: Determine Type of Target Object) In step S2041, the determining unit 115 determines whether the target object is the aortic valve or the mitral valve using the type information of the target object which the type information acquiring unit 113 acquired in step S202. The determining unit 115 advances processing to step S2042 if the target object is the mitral valve, or to step S2043 if the target object is the aortic valve.

(Step S2042: Determine Probe Angle) In step S2042, assuming that the target object is the mitral valve, the determining unit 115 determines the observation surface in accordance with the probe angle information which the probe angle acquiring unit 114 acquires in step S203.

Here the relationship between the probe angle of the probe in the trans-esophageal echocardiography and the anatomical structure will be described with reference to FIG. 7A to FIG. 7C. The movable range of the probe is narrower in the trans-esophageal echocardiography compared with the case of the trans-thoracic echocardiography, since the probe passes through the esophagus. Therefore in the case of imaging a target object inside the body using the probe in the trans-esophageal echocardiography, the probe position and the probe angle are more restricted compared with the case of the case of trans-thoracic echocardiography.

Figure 7A:
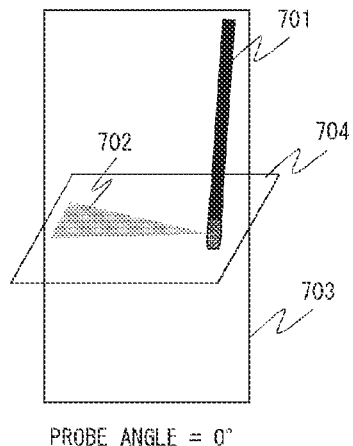
FIG. 7A to FIG. 7C are diagrams depicting a relationship between a probe angle and an anatomical structure in trans-esophageal echocardiography.
Figure 7B:
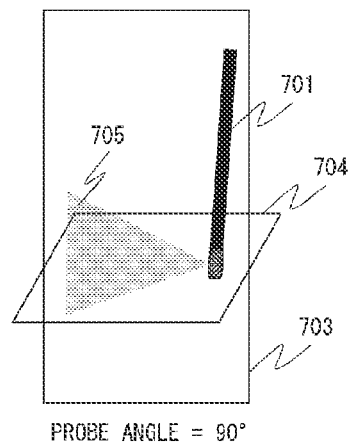

FIG. 7A and FIG. 7B are schematic diagrams depicting a relationship between the rotation angle (probe angle) of the scan surface at the probe end portion 701 and scan ranges 702 and 705 which indicate the standard plane to be the observation surface. FIG. 7A indicates a case where the probe angle is 0°, and FIG. 7B indicates a case where the probe angle is 90°. In FIG. 7A and FIG. 7B, a virtual plane 703, which includes the probe end portion 701, and a virtual plane 704, which is orthogonal to the plane 703, are assumed to exist. As illustrated in FIG. 7A, if the probe angle is 0°, the scan range 702 of the probe is set within the plane 704. Further, as illustrated in FIG. 7B, if the probe angle is 90°, the scan range 705 of the probe is set within the plane 703.

Figure 7C:
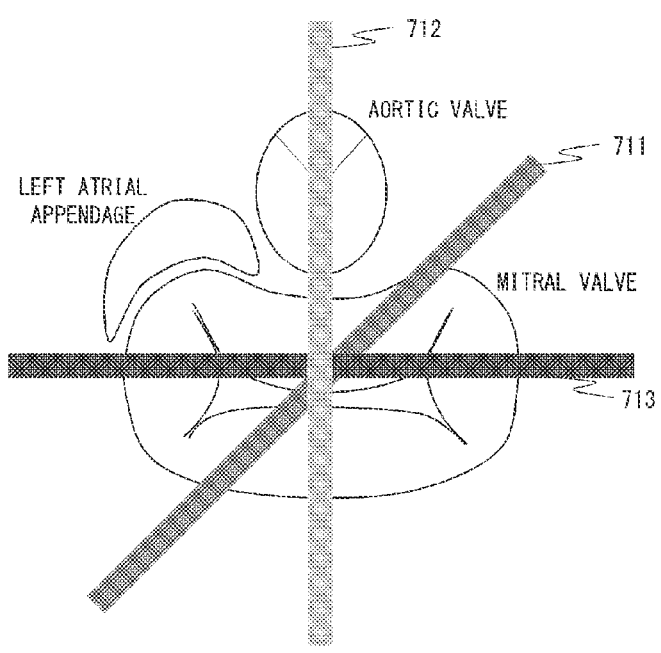

FIG. 7C is a schematic diagram depicting a relationship between the probe angle in the mitral valve analysis of the trans-esophageal echocardiography and the standard plane to be the observation surface. Since the probe end portion 701 is located on the left atrium side, FIG. 7C is a schematic diagram depicting the mitral valve viewed from the probe end portion 701 side (left atrium side). Therefore in FIG. 7C, the extending direction of the probe end portion 701 and the page surface direction are parallel with each other. In FIG. 7C, a left atrial appendage exists at the upper left of the mitral valve. This field of view, which is the same as the view of the mitral valve that a surgeon observes during surgery, is called the "surgeon's view".

As indicated by the scan ranges 702 and 705 of the probe end portion 701 in FIG. 7A and FIG. 7B, one plane (cross-section) of the target object is imaged as a standard plane, hence if the probe angle is approximately 0°, the standard plane 711 becomes the observation surface. If the probe angle is approximately 45° to 60° the standard plane 712 becomes the observation surface. If the probe angle is approximately 135°, the standard plane 713 becomes the observation surface. The standard planes 712 and 713 correspond to the standard planes 303 and 304 indicated in FIG. 2 respectively. The relationship between the probe angle and the standard plane differs depending on the test subject, hence the relationship between the probe angle and the standard plane is not limited to the above mentioned relationship.

As described above, the observation surface can be determined depending on whether the probe angle is 90° or more or less than 90°, utilizing the fact that each standard plane is approximately orthogonal to each other. In the present embodiment, the determining unit 115 determines that the observation surface corresponds to the standard plane 303 (representative plane) if the probe angle is 90° or more (S2045). The determining unit 115 determines that the observation surface corresponds to the standard plane 304 (non-representative plane) if the probe angle is less than 90° (S2044). In this way, the determining unit 115 determines the observation surface, that is, the type of the orientation of the target object based on the probe angle. However, the predetermined angle (90°) to be a threshold of the probe angle used for determining the observation surface may be another angle if the observation surface can be determined as described above.

(Step S2043: Determine Probe Angle) In step S2043, assuming that the target object is the aortic valve, the determining unit 115 determines the observation surface based on the probe angle. Normally if the probe angle is approximately 135°, the standard plane 403 becomes the observation surface, and if the probe angle is approximately 25° to 45°, the standard plane 405 becomes the observation surface. In the present embodiment, the determining unit 115 determines that the observation surface corresponds to the standard plane 403 (representative plane) if the probe angle is 90° or more (S2047). The determining unit 115 determines that the observation surface corresponds to the standard plane 405 (non-representative plane) if the probe angle is less than 90° (S2046). In this way, the determining unit 115 determines the observation surface, that is, the type of the orientation of the target object, based on the probe angle. However, the threshold (90°) of the probe angle used for determining the observation surface may be another angle if the observation surface can be determined as described above, similar to the case of the observation of the mitral valve. By a series of processing steps in S2042 to S2047, the determining unit 115 can determine the orientation of the observation surface, that is, the type of the orientation of the target object, among the directions including the representative direction and at least one non-representative direction.

(Step S2048: Display Determination Result) In step S2048, on the display unit 161, the display processing unit 151 displays information, on the orientation of the target object or on the standard plane determined as the observation surface. The control unit 111 may store the information on the standard plane, which was determined as the observation surface, as the meta information of the input image, or may store the information in the storage unit 131. The display processing of the information on the standard plane in step S2048 is not essential. Therefore in step S2048, the control unit 111 may simply store the information on the standard plane, which was determined as the observation surface, in the storage unit 131, the database 102, or the random access memory (RAM) which is not illustrated.

(Step S205: Correct Image) Referring back to FIG. 5, in step S205, the correcting unit 116 executes input image correction processing to align the orientation of the target object in the input image with the representative direction based on the standard plane determined by the determining unit 115. Specifically, a representative plane (cross-section) is defined for each target object in advance, hence the correcting unit 116 rotates the input image based on the determined standard plane, so that the representative plane is located on the observation surface in the input image.

In the present embodiment, the standard plane 303 used for the mitral valve analysis and the standard plane 403 used for the aortic valve analysis are defined as the representative plane of each analysis. For example, it is assumed that the type of the target object is the mitral valve, and the observation surface determined by the determining unit 115 is the standard plane 304. In this case, the correcting unit 116 executes the processing to rotate the input image, so that the standard plane 303, which is the representative plane, is located on the observation surface.

Specifically, when the observation surface is the X-Y plane and the Y axis is the vertical direction, the correcting unit 116 rotates the input image with the Y axis as the rotation axis. In the mitral valve analysis, the orientation of the target object in the input image can be aligned with the representative direction by rotating the input image 90° counterclockwise.

In the same manner, it is assumed that the type of the target object is the aortic valve, and the observation surface determined by the determining unit 115 is the standard plane 405. In this case, the correcting unit 116 executes the processing to rotate the input image, so that the standard plane 403, which is the representative plane, is located on the observation surface. In the case of the aortic valve analysis, the input image is often displayed or saved with setting the coordinate axes such that the aortic valve comes to the right side of the mitral valve on the observation surface. Therefore by rotating the input image 90° clockwise, the correcting unit 116 can align the orientation of the target object in the input image with the representative direction. The rotation angle is not limited to 90°, but may be 270° counterclockwise, or may be a rotation angle determined based on the probe angle.

(Step S206: Estimate Standard plane) Then in step S206, the standard plane estimating unit 117 performs a standard plane estimating processing on the input image after the correction by the correcting unit 116. The standard plane estimating processing is an example of a predetermined processing related to the analysis. The observation surface determined by the determining unit 115 is for determining a general orientation of the target object, and may not always be an appropriate observation surface for various measurements of an analysis. For example, in the mitral valve analysis, each feature value of the mitral value is more easily searched if the center of the input image matches with the centers of the three standard planes, and each standard plane is parallel with a different one of the X, Y and Z axes which are orthogonal to each other. Further, after merely performing the correction processing on the input image by the correcting unit 116, the center of the input image and the centers of the standard planes may deviate, or the standard planes may be inclined from the axes. As a result, each feature value of the mitral valve in the input image may not be searched correctly. Therefore in the present embodiment, the standard plane estimating unit 117 executes a preferable standard plane estimating processing. A similar estimating processing may also be performed for the standard planes other than the standard plane, which is the observation surface determined by the determining unit 115, since each of these standard planes may not be orthogonal to the observation surface.

In the present embodiment, the orientation of the target object in the input image is aligned with the representative direction by the correction of the input image in step S205. Thereby the search range in the standard plane estimating processing in this step can be narrowed down compared with the case where the orientation of the target object is not aligned with the representative direction. Further, the range of the parameters used for searching the target object in the input image, such as the search range of the center coordinates and the rotation range of the axis, can be narrowed down. The parameters used for the search may be read from the storage unit 131 or the database 102, or may be inputted by the user via the operation unit 141.

For the estimating processing by the estimating unit 117, a decision tree, such as a random forest, may be used, or a convolutional neural network (CNN), which is a form of neural network, may be used.

For example, an estimating processing using a random forest will be described. A plurality of learned decision trees are provided, then all or a part of the input image is extracted, and the extracted image is inputted into the decision trees. In a decision tree, in accordance with a branching condition determined by learning in advance, a parent node (input source) is sorted into child nodes (sorting destinations). A final child node which can no longer be sorted is called a "leaf". The estimation result is determined by a score value (class value) of the leaf. The estimation processing using a plurality of decision trees is normally called ensemble learning, and determines the final sorting result by taking the majority decision for the output results of the decision trees, which are individually learned. Compared with a case of using one high performance classifier (identifier), the performance to handle variations of the sorting targets (scalability) improves if the majority decision is determined using a plurality of classifiers having the average performance (weak classifiers).

In the learning by the estimating unit 117 corresponding to the learning unit of the present embodiment, the correcting unit 116 aligns the orientation of the target object in the input image with the representative direction. In this learning, the scalability to support various images normally improves the higher the number of learning samples. In order to provide many learning samples during learning, the rotation processing of the image may be performed using random rotation angles in the padding operation, in order to increase the image data of the planes (cross-sectional image) of the target object. For example, in the case of padding of the correct answer samples, the image data is generated by performing rotation processing on the images having the planes (cross-sectional images) of the target object at a rotation angle within a range where the orientation of the target object is regarded as aligned with the representative direction. In the case of padding the incorrect answer samples, the image data is generated by performing rotation processing on the images having the planes (cross-sectional images) of the target object at the rotation angle, excluding the above mentioned range where the orientation of the target object is regarded as aligned with the representative direction.

(Step S207: Display Estimation Result) In step S207, the display processing unit 151 displays the standard plane, estimated by the estimating unit 117, on the display unit 161. Instead of or in addition to the display of the standard plane by the display processing unit 151, information on the estimated standard plane may be stored in the storage unit 131.

In the present embodiment, by executing the above processing steps, the image processing apparatus 101 determines the standard plane to be the observation surface of the input image, based on the type of the target object and the probe angle when the image was captured, whereby a general orientation of the target object in the input image can be determined. Then the image processing apparatus 101 corrects the input image based on the type of the target object in the input image, so that the orientation of the target object is aligned with the representative direction, and performs the standard plane estimating processing on the corrected input image. Therefore according to the present embodiment, the orientation of the target object is aligned with the representative direction, and as a result, the search range in the standard plane estimating processing can be narrowed down, and a higher accuracy in estimated solutions can be expected.

Second Embodiment

Second Embodiment of the present disclosure will be described next. Similar to First Embodiment, an image processing apparatus according to Second Embodiment determines the type of the orientation of the target object in the input image. In the first embodiment, the type of orientation of the target object is determined using the probe angle and the type information of the target object. However, as the method for determining the type of orientation of the target object, a method of determining the type of orientation of the target object by estimating the type based on machine learning of the planes of the image, for example, may be used.

In the present embodiment, the control unit, the determining unit and the correcting unit of the image processing apparatus are different from the control unit 111, the determining unit 115 and the correcting unit 116 of First Embodiment. Furthermore, the determining processing to determine the type of the orientation of the target object executed by the image processing apparatus, that is, the observation surface determining processing is different from the processing in step S204 of First Embodiment. In the following description, aspects different from First Embodiment will primarily be described, and a configuration or processing the same as First Embodiment will be denoted with a same reference sign, for which detailed description will be omitted.

Figure 8:
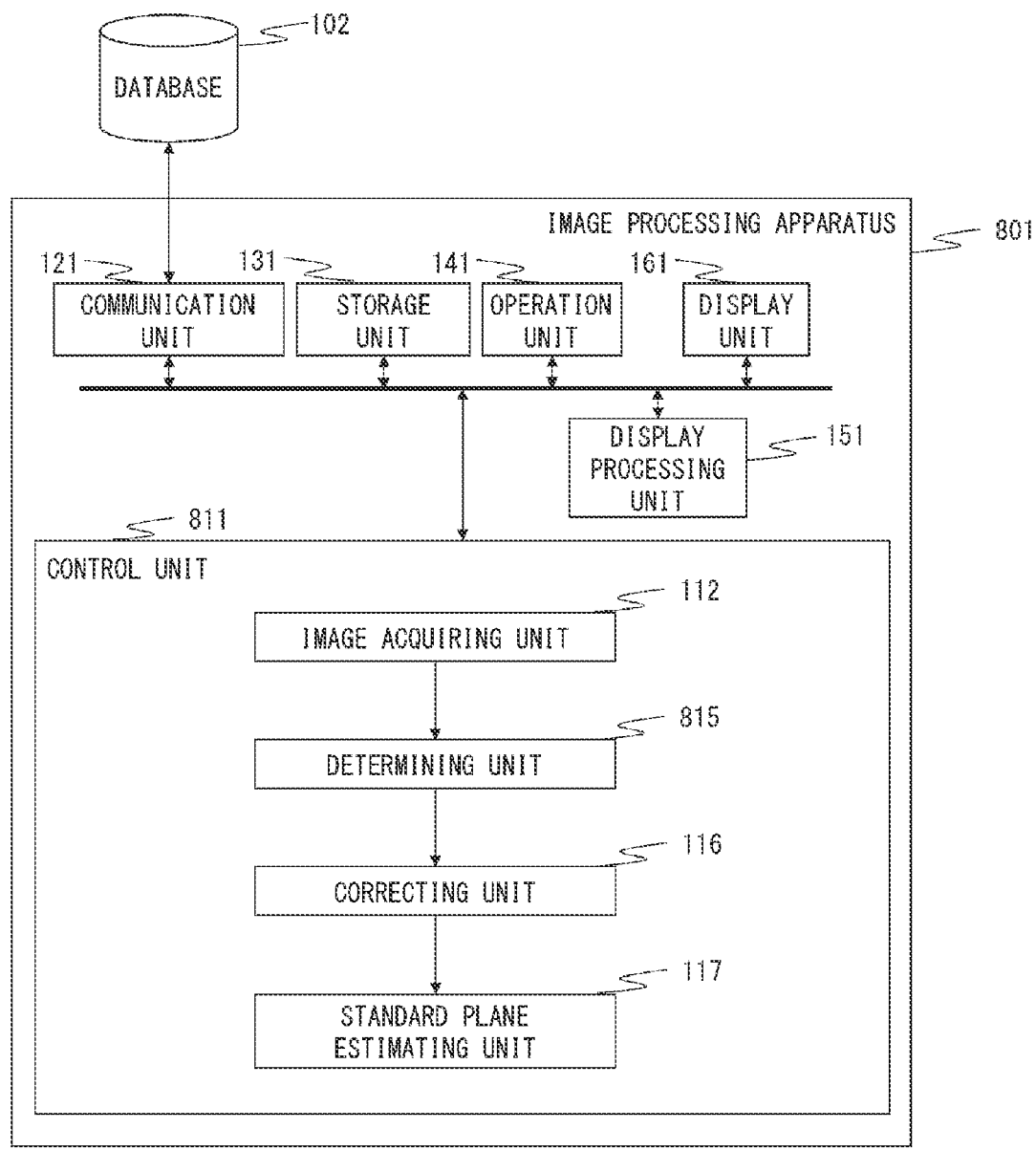
FIG. 8 is a block diagram depicting another configuration example of the image processing system according to an embodiment.

FIG. 8 is a block diagram depicting a general configuration of the image processing apparatus 801 according to Second Embodiment. As indicated in FIG. 8, a control unit 811 of the image processing apparatus 801 includes an image acquiring unit 112 that acquires an input image, and a determining unit 815 that determines the type of the orientation of the target object of the input image. Further, the control unit 811 includes the correcting unit 116 that performs the input image correcting processing, so that the orientation of the target object aligns with the representative direction, and the standard plane estimating unit 117 that estimates the standard plane from the input image connected by the correcting unit 116.

(Step S204: Determine Type of Orientation of Target Object) After the image processing apparatus 801 executes the processing in steps S201 to S203 in FIG. 5, the determining unit 815 determines in step S204 the type of the orientation of the target object of the input image acquired by the image acquiring unit 112 using the learned determiner. In Second Embodiment, CNN is used as an example of the determiner.

Figure 9:
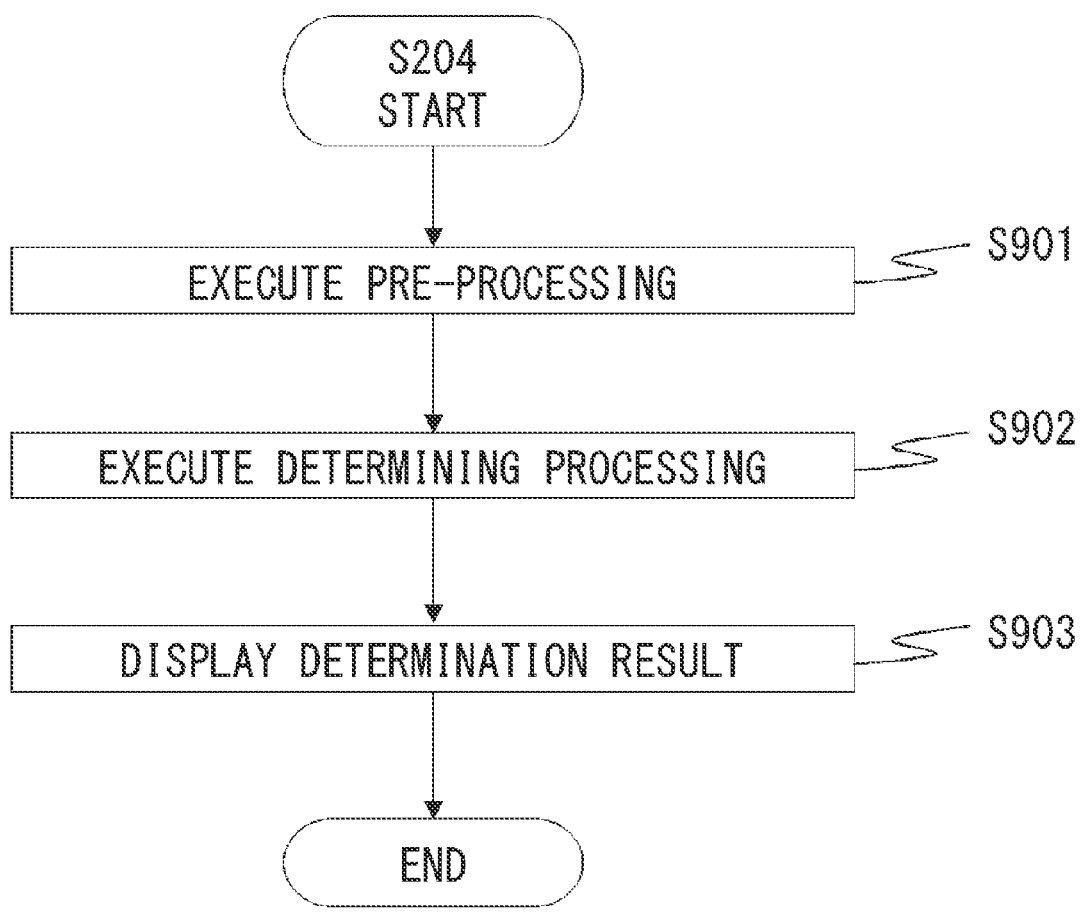
FIG. 9 is a flow chart of the processing steps executed by the image processing apparatus according to an embodiment.

The processing of determining the type of the orientation of the target object in the input image by the determining unit 815 will be described with reference to the flow chart in FIG. 9. In Second Embodiment, the image processing apparatus 801 executes the sub-routine indicated in FIG. 9, instead of the sub-routing indicated in FIG. 6.

(Step S901: Execute Pre-Processing) In step S901, the determining unit 815 executes the pre-processing of the image so as to input the input image to the determiner. Specifically, the determining unit 815 extracts a plane, for determining the type of the orientation of the target object, from the input image acquired by the image acquiring unit 112. Here the extracted plane becomes the observation surface.

(Step S902: Execute Determining Processing) In step S902, the determining unit 815 determines the type of the orientation of the target object in the input image acquired by the image acquiring unit 112. First the determining unit 815 inputs the input image, which was pre-processed in step S901, to CNN, which is a determiner which has already learned the type of orientation of the target object. Using the learned CNN, various processing operations (e.g. convolution, magnification, demagnification, combining) specified as a model are performed on the input image, and features are extracted from the input image. The majority is determined in all the combined layers based on the extracted features, and a value, to indicate the probability of the orientation of the target object, is outputted.

(Step S903: Display Determining Result) In step S903, the display processing unit 151 displays information, which indicates the type of the orientation of the target object determined by the determining unit 815, on the display unit 161. Instead of or in addition to the display of the determination result by the display processing unit 151, information indicating the determined type of the orientation of the target object may be stored in the storage unit 131 or the like. When the processing in step S903 completes, the image processing apparatus 801 executes the processing steps S205 to S207 indicated in FIG. 5.

In Second Embodiment, a total of six standard planes of the mitral valve and the aortic valve exist, hence 6 classes of probability are outputted respectively, and the class having the highest value may be used as the type of the orientation of the target object. At this time, an identifier to identify the type of the orientation may be constructed in advance for each target type (mitral valve or aortic valve), so that the orientation is identified using the identifier in accordance with the target type information acquired by the type information acquiring unit 113. In this case, the type of the orientation of the target object may be determined by outputting the probabilities of three planes of the standard plane. Here for the model of the CNN, an arbitrary model may be used, such as VGG16 which is a publicly known model, or a model to extract features from the input image and a model to be used for all of the combined layers, may be used separately, or publicly known models may be combined arbitrarily. In the case of using VGG16, a number of channels of an input image is specified to three, but this model may be changed. Further, in the case of using VGG16, the same images may be combined in the channel direction and inputted, or three different images, that are acquired by changing the position to extract the input image, may be inputted instead of the same images.

CNN learning is performed using the image of any one of the standard planes of the input image and the attached information (label) to distinguish the standard plane for the plane image (cross-sectional image) of the target object. For the label, a relationship of the standard plane and the class is set in a matrix if a 6-class classification is used. For example, in a case of a 1×6 matrix, the standard plane 303 is assigned to the first column, the standard plane 304 is assigned to the second column, and the standard plane 305 is assigned to the third column. In the same manner, the standard planes 403 to 405 are assigned to the fourth to sixth columns respectively. For example, in a case of an image of which one learning case is the standard plane 303, the label is [1, 0, 0, 0, 0, 0]. Then the plane image of the target object is inputted to the CNN, the outputted probability of each class and the values of the label are captured, and the parameters of the CNN are adjusted so as to minimize error. Thereby a learned model, to output information which indicates whether the type of the orientation of the target object is the representative direction or the non-representative direction, can be acquired using the plane image of the target object as an input. In Second Embodiment, two planes are generated as the standard plane in the non-representative direction. Therefore if it is determined that the type of the orientation of the target object is the non-representative direction, information on the determined non-representative direction is held. Using a known method, the correcting unit 116 performs the rotation processing, to correct the image in the representative direction, on the image in accordance with the information indicating the non-representative direction.

In the above mentioned example, the two-dimensional image is extracted from the three-dimensional image, but the three-dimensional image may be directly inputted to the CNN. As the convolution processing performed in CNN, the one-dimensional convolution, the two-dimensional convolution and the three-dimensional convolution, which considers the depth direction, are well known. Therefore the image to be inputted to the CNN need not be limited to a two-dimensional image. If the type of the orientation of the target object is determined in this case, the observation surface observed on the X-Y plane, for example, may be used for determination.

In the above description, CNN is used, but any technique may be used as long as the type of the orientation of the target object can be determined. For example, instead of CNN, the random forest described in First Embodiment may be used, or a classifier, such as the support vector machine (SVM), may be used. As long as the technique employs statistical analysis, the back projection for lost pixels (BPLP) method, which is a technique known in Toshiyuki Amano, et. al. "An appearance based fast linear pose estimation" MVA 2009 IAPR Conference on Machine Vision Applications, 2009 May 20-22, may be used.

According to the image processing apparatus 801 of Second Embodiment, using a learned model, where a plane image (cross-sectional image) of the target object is inputted and where information to indicate whether the type of the orientation of the target object is the representative direction or the non-representative direction is outputted, the type of the orientation of the target object based on the machine learning is estimated. Thereby the standard plane can be accurately estimated for the input image.

Third Embodiment

Third Embodiment of the present disclosure will be described next. Similar to Embodiments 1 and 2, an image processing apparatus according to Third Embodiment corrects the input image based on the type of the orientation of the target object. In First Embodiment, rotation processing is performed on an image, which the correcting unit 116 determined that the type of the orientation of the target object is different, whereby the search range in the standard plane estimating processing by the standard plane estimating unit 117 can be narrowed down. However, the search range can be narrowed down not only by performing the rotation processing on the image, but also by rotating the standard plane and the image relative to each other using the information on the type of the orientation of the target object in the standard plane estimating processing. In the following description, aspects different from First Embodiment will be primarily described, and a configuration or processing the same as First Embodiment will be denoted with a same reference sign, for which detailed description will be omitted.

Figure 10:
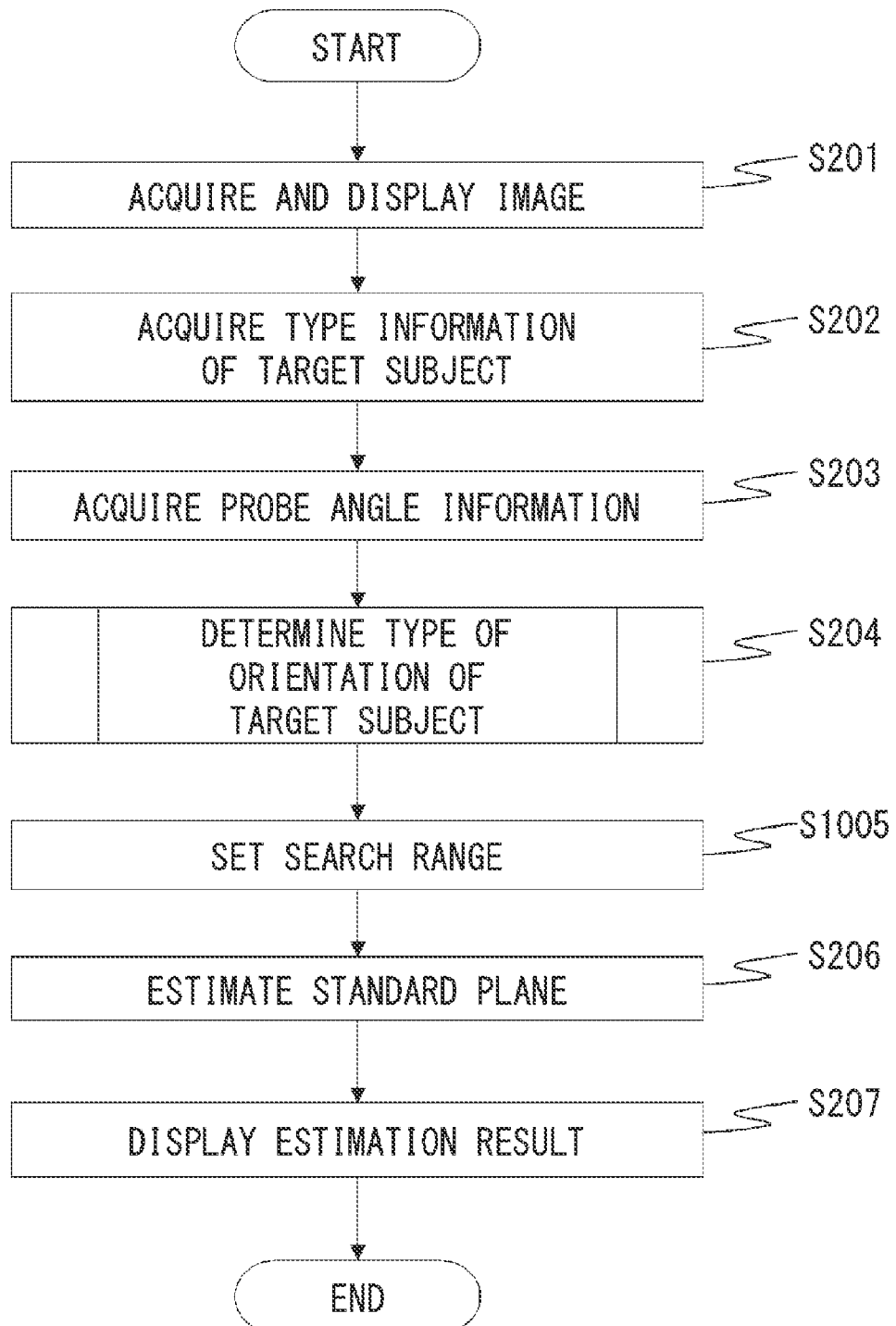
FIG. 10 is a flow chart of the processing steps executed by the image processing apparatus according to an embodiment.

An example of the processing executed by the image processing apparatus 101 according to Third Embodiment will be described with reference to the flow chart in FIG. 10. In Third Embodiment, the image processing apparatus 101 executes the processing steps of the flow chart indicated in FIG. 10, instead of the processing steps of the flow chart indicated in FIG. 5. In the flow chart of FIG. 10, the processing steps in S201 to S205, S206 and S207 are the same as the corresponding processing steps in FIGS. 5 and 6, hence detailed description thereof is omitted here.

(Step S1005: Set Search Range) In step S1005, the correcting unit 116 sets a search range that is used for the standard plane estimating processing by the standard plane estimating unit 117. Unlike First Embodiment, the correcting unit 116 does not perform the rotation correction on the input image. The correcting unit 116 determines the search range based on the information on the type of the orientation of the target object in order to narrow down the search range.

In First Embodiment, a predetermined search range, which is determined based on the distribution of the angle formed by a normal vector of the standard plane and each reference axis, and the like. However, depending on the purpose of the analysis, the search range may be dynamically changed in accordance with the orientation of the standard plane. For example, in a case where it is determined that the type of the orientation of the target object is the representative direction, the predetermined search range is used, and in a case where it is determined that the type of the orientation of the target object is the non-representative direction, the search range is changed by dynamically changing the coordinate system to determine the search range.

For example, in a case where it is determined that the type of the orientation of the target object is the non-representative direction, during the mitral valve analysis, the X axis component and the Z axis component of a predetermined search range are switched, and the +/− sign of each component is adjusted in accordance with the orientation of the reference axis. Unlike the processing to rotate the image, the change of the signs need to be considered when the search range, of which axes are determined, is changed.

Figure 11:
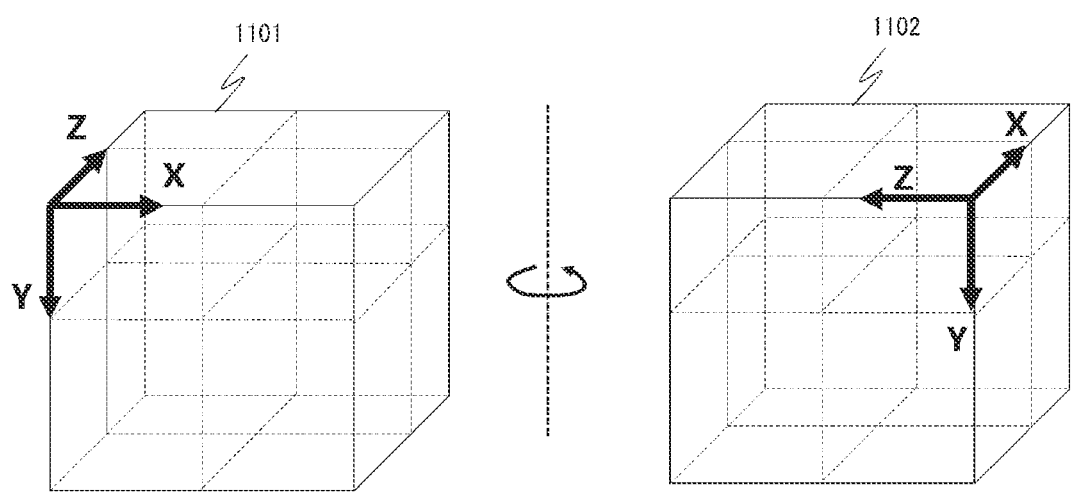
FIG. 11 is a diagram depicting an influence of a coordinate change caused by rotation according to an embodiment.

Adjustment of the signs of the axis components in the search range will be described with reference to FIG. 11. A coordinate system 1101 indicated at the left of FIG. 11 will be described as an example. When counterclockwise rotation (arrow direction indicated in FIG. 11) is performed with the Y axis as the rotation axis in the mitral valve analysis, the coordinate system 1101 becomes a coordinate system 1102 as a result of the rotation. Here in the coordinate systems 1101 and 1102, the sign of the Y axis component does not change because the Y axis and the rotation axis are the same. The X axis of the coordinate system 1101 is handled as the Z axis of the coordinate system 1102 after rotation, but the sign of the axis component is not inverted since the orientation of the axis is unchanged before and after rotation. However, the Z axis of the coordinate system 1101 is handled as the X axis of the coordinate system 1102 after rotation, and the sign of the axis component needs to be inverted since the positive direction of the Z axis after rotation corresponds to the negative direction of the X axis before rotation.

In step S206, the standard plane estimating unit 117 performs the standard plane estimating processing on the input image, using the search range after the signs of the axis components are adjusted by the processing in step S1005.

According to Third Embodiment, the image processing apparatus 101 executes the above mentioned processing steps, and by adjusting the sign of each axis component in the coordinate system of the search range, without correcting the rotation of the input image, the orientation of the target object in the input image can be aligned with the representative direction based on the type of the target object. Then in the search range that is set in the input image in accordance with the orientation of the target object, the standard plane estimating unit 117 estimates the standard plane in the input image. Thereby, similar to Embodiments 1 and 2, the operation amount in the standard plane estimating processing is reduced, and the accuracy of the estimated solution is expected to improve.

Embodiments of the present disclosure have been described, but the technique of the present disclosure is not limited to the above embodiments, but may be changed, and/or modified in various ways within the technical scope disclosed in the claims. Modifications of the above mentioned embodiments will be described herein below. In the following description, a configuration or processing the same as the above embodiments are denoted with a same reference sign, for which detailed description is omitted.

First Modification

In First Embodiment, it is assumed that the image processing apparatus 101 processes one of the inputted images of the mitral valve and the aortic valve. However, the above configuration and processing are applicable even in a case where the image processing apparatus 101 performs image processing only for the mitral valve or only for the aortic valve.

In the case of analyzing only the mitral valve or only the aortic valve, the type of the orientation of the target object can be determined based on the probe angle. The rotation angle corrected by the correcting unit 116 to align the type of the orientation of the target object with the representative direction, is 90°. However, similar to the case of step S205, the rotation angle is not limited to 90°.

Furthermore, in the image processing apparatus 101 the above configuration and processing are also applicable to the standard plane estimating processing, even in a case where image processing is performed on a target object of the trans-esophageal echocardiography other than the mitral calve and the aortic valve.

Second Modification

In First Embodiment, the image processing apparatus 101 estimates the standard plane by executing the processing in step S206, but the processing executed in step S206 is not limited to estimation of the standard plane, but may be a different processing.

For example, an arbitrary analysis processing may be performed on an inputted image of which orientation of the target object is aligned to the representative direction. For example, the present disclosure may be applicable to the processing to analyze the state of the backflow of blood or the state of the stricture due to the poor opening of valves, in the case of a valvular insufficiency caused by a valvular disease of the mitral valve, may be performed. For the analysis of such a state, trans-esophageal echocardiology is normally performed, where the standard plane of the input image is analyzed, and the problematic region is specified.

For example, by analyzing the standard plane 304, both ends of the posterior cusp and the center portion of the anterior cusp can be analyzed. By analyzing the standard plane 303, on the other hand, the center portions of the anterior cusp and the posterior cusp can be analyzed. In this way, it is critical to determine which standard plane is being analyzed, in order to specify a problem atrial region, hence processing to align the orientation of the target object in the input image with the representative direction. The heart functions or the like may be analyzed as well.

Furthermore, without performing analysis processing on the input image in which the orientation of the target object is aligned with the representative direction, this input image may be stored in the storage unit 131 or in the database 102, or may be displayed on the display unit 161 by the display processing unit 151. Furthermore, without performing the rotation correction by the correcting unit 116, the information to indicate the type of the orientation of the target object may be attached as meta information, a header file or the like of the image, and stored in the storage unit 131 or the database 102, or displayed on the display unit 161.

Third Modification

In Third Modification, the image processing apparatus 101 is directly integrated in the inspection device, or the image processing apparatus 101 is connected to the inspection device, so as to process the captured input image in real-time and determine the type of the orientation of the target object. In this case, the type of the orientation of the target object may be notified to the user by displaying the determination result on the display unit 161, or the type of the orientation of the target object may be attached to the analysis result as attachment information when the analysis result is recorded to the storage unit 131 or the database 102.

Other Embodiments

The technique of the present disclosure may be implemented as a system, an apparatus, a method, a program, a recording medium (storage medium) or the like. Specifically, the present disclosure may be applied to a system constituted of a plurality of devices (e.g. host computer, interface device, imaging apparatus, web application), or may be applied to an apparatus constituted of one device.

Needless to say, the object of the present disclosure is implemented by the following procedure. That is, a recording medium (or a storage medium) recording program codes of software (computer programs) to implement the functions of the above mentioned embodiments is supplied to a system or an apparatus. This storage medium is a computer-readable storage medium. Then the computer (or CPU or MPU) of the system or the apparatus reads and executes the program codes stored in the recording medium. In this case, the program codes read from the recording medium implement the above mentioned functions of the embodiments, and the recording medium recording the program codes constitute the technique of the present disclosure.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present disclosure, the operation amount is reduced in the standard plane estimating processing in an image, and the accuracy to estimate the standard plane can be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-082419, filed on May 14, 2021, which is hereby incorporated by reference herein in its entirety.

What is claimed is:

1. An image processing apparatus comprising:
   at least one memory storing a program; and
   at least one processor which, by executing the program, causes the image processing apparatus to:
   acquire three-dimensional ultrasonic image of a heart of a test subject including a plurality of target objects, the three-dimensional ultrasonic image being imaged from an esophagus of the test subject by a three-dimensional ultrasonic probe for trans-esophageal echocardiography inserted into the test subject;
   acquire type information indicating one of the plurality of target objects;
   acquire angle information indicating a rotation angle of a scan face of the three-dimensional ultrasonic probe; and
   perform correction to rotate the three-dimensional ultrasonic image so that an orientation of the one of the plurality of target objects in the three-dimensional ultrasonic image aligns with a representative direction based on the type information and the angle information.

2. The image processing apparatus according to claim 1, wherein
   the at least one processor causes the image processing apparatus to:
   determine whether the orientation of the one of the plurality of target objects in the three-dimensional ultrasonic image is the representative direction or a non-representation direction based on the type information and the angle information, and
   the correction is performed in a case where the determined orientation of the one of the plurality of target objects is the non-representative direction, and the correction is not performed in a case where the determined orientation of the one of the plurality of target objects is the representative direction.

3. The image processing apparatus according to claim 2, wherein
   the at least one processor causes the image processing apparatus to determine whether the orientation of the one of the plurality of target objects is the representative direction or the non-representative direction by comparing the angle information and angle information associated with the type information.

4. The image processing apparatus according to claim 1, wherein
   the plurality of target objects include a mitral valve and an aortic valve, and
   the at least one processor causes the image processing apparatus to acquire type information of the mitral valve or the aortic valve by specified by a user.

5. The image processing apparatus according to claim 1, wherein
   the at least one processor causes the image processing apparatus to estimate three standard planes that are approximately orthogonal to each other for the three-dimensional ultrasonic image after the correction, and
   the three standard planes are used for observation of the one of the plurality of target objects.

6. An image processing method comprising steps of:
   acquiring a three-dimensional ultrasonic image of a heart of a test subject including a plurality of target objects, the three-dimensional ultrasonic image being imaged from an esophagus of the test subject by a three-dimensional ultrasonic probe for trans-esophageal echocardiography inserted into the test subject;
   acquiring type information indicating one of the plurality of target objects;
   acquiring angle information indicating a rotation angle of a scan face of the three-dimensional ultrasonic probe; and
   performing correction to rotate the three-dimensional ultrasonic image so that an orientation of the one of the plurality of target objects in the three-dimensional ultrasonic image aligns with a representative direction based on the type information and the angle information.

7. A non-transitory computer readable medium that stores a program, wherein the program causes a computer to execute:

acquiring three-dimensional ultrasonic image of a heart of a test subject including a plurality of target objects, the three-dimensional ultrasonic image being imaged from an esophagus of the test subject by a three-dimensional ultrasonic probe for trans-esophageal echocardiography inserted into the test subject; and acquiring type information indicating one of the plurality of target objects;

acquiring angle information indicating a rotation angle of a scan face of the three-dimensional ultrasonic probe; and performing correction to rotate the three-dimensional ultrasonic image so that an orientation of the one of the plurality of target objects in the three-dimensional ultrasonic image aligns with a representative direction based on the type information and the angle information.

* * * * *